(12) United States Patent
Sacco

(10) Patent No.: US 7,618,235 B2
(45) Date of Patent: Nov. 17, 2009

(54) DISPOSABLE SPIROMETER WITH PLASTIC INJECTION MOULDED TURBINE

(75) Inventor: Paolo Boschetti Sacco, Rome (IT)

(73) Assignee: MIR S.R.L., Rome (IT)

( * ) Notice: Subject to any disclaimer, the term of this patent is extended or adjusted under 35 U.S.C. 154(b) by 417 days.

(21) Appl. No.: 10/573,899

(22) PCT Filed: Feb. 18, 2004

(86) PCT No.: PCT/IT2004/000068

§ 371 (c)(1),
(2), (4) Date: Mar. 29, 2006

(87) PCT Pub. No.: WO2005/037102

PCT Pub. Date: Apr. 28, 2005

(65) Prior Publication Data

US 2007/0059165 A1    Mar. 15, 2007

(30) Foreign Application Priority Data

Oct. 22, 2003   (IT)   .......................... RM2003A0487

(51) Int. Cl.
*A61B 5/09* (2006.01)

(52) U.S. Cl. .................. 415/121.3; 415/915; 73/861.89; 600/539

(58) Field of Classification Search ................. 600/539; 73/861.89, 861.33, 861.85; 416/61; 415/912, 415/9, 193, 915

See application file for complete search history.

(56) References Cited

U.S. PATENT DOCUMENTS 4,733,570 A * 3/1988 Peters ...................... 73/861.33
5,732,709 A * 3/1998 Tacklind et al. ............. 600/539

FOREIGN PATENT DOCUMENTS

EP      0 369 506      5/1990

* cited by examiner

*Primary Examiner*—Richard Edgar
(74) *Attorney, Agent, or Firm*—Young & Thompson

(57) ABSTRACT

A small dimension throwaway turbine device for checking the breathing flux, to be used in spirometric instruments, allowing an extreme simplification in project and realization, and comprises a turbo-turbine (4) with an inlet deflector (1) and an outlet deflector (3), and a single-piece mobile equipment comprising a blade (2) and a rotation axis (5), realized out of one single raw material.

6 Claims, 1 Drawing Sheet

DISPOSABLE SPIROMETER WITH PLASTIC INJECTION MOULDED TURBINE

The present invention concerns a small dimension turbine device for checking the breathing flux, to be used in spirometric instruments, for allowing an extreme simplification in project and realization, as said turbine is realized in one single construction phase, making use of one single, low cost raw material, so as to make possible a throwaway use.

BACKGROUND OF THE INVENTION

It is known that the technique of the spirometric measuring, i.e. the analysis of the breathing functionality, always provides a tester of the inspired and expired air volume or of the speed or flux of the same. Usually, a device transforming the primary measuring obtained by the testing is transformed into an electric signal by a device provided downstream of the tester.

The most commonly used physical phenomena onto which the flux tester are based are two: the one exploiting the pressure determined at the passage of a fluid according to the Venturi principle, and the one that obtains the measuring of the air volume from the rotation of a turbine placed in between the flux.

DESCRIPTION OF THE RELATED ART

The tester devices known at present, working according to the principle of the turbine, are only of the kind thought for a use for multiple tests and comprise:
  a turbine pipe of infrared ray transparent polycarbonate, provided with an inlet deflector for obtaining the rotation of the air passing through the pipe;
  a mobile equipment consisting of a blade with a metal rotation axis;
  two cavities out of semi-precious stones, like a synthetical sapphire, wherein the metal axis is housed and wherein it may rotate with low friction;
  two adjusting screws of said cavities;
  an outlet deflector out of polycarbonate, having the same function than the inlet deflector.

Above mentioned components require assembling phases in under-assembling, as blade and axis, adjusting screw and cavity out of synthetic sapphire cavity, which—once assembled—provide the turbine flux tester of known kind, the functioning whereof may be described as follows:

the mobile equipment rotates at a speed directly proportional to the speed of the expired or inspired air, and said rotation is taken by two couples of infrared emitters/sensors which generate impulses in a number proportional to the quantity of air that passes through the turbine pipe.

As during a spirometric test the speed of the turbine may reach peaks of 1000 revolutions per second, even if only for few fractions of a second, the metal axis onto which the blade is mounted is out of a special alloy, and the rotation movement is supported by two semi-precious stones, i.e. as already mentioned two synthetic sapphires. For both said elements—axis and semi-precious stones—components of watchmaking must be used, because until now they have proved to be the sole that have permitted to assure the required measuring precision for the spirometric device to stand the severe standards provided for spirometric tests. Due to the use of said precious components, modifications of the response—typical of the tester and due to the wear of the parts—may be eliminated. Furthermore, as the measuring performed with that kind of tester, on the contrary of others based onto different principles, is not influenced by the surrounding conditions, the turbine flux tester realizes a highly accurate measuring system, reliable and that does not require calibration. This kind of tester may therefore be used for a high number of spirometric tests without any decay of the result quality, and needs, at the end of each test, to be sterilized for assuring the hygiene.

As an alternative, throwaway antibacterial filters may be used coupled at the entrance of the turbine pipe, while the use of a throwaway mouthpiece is always necessary, because it gets into contact with the mouth of the patient.

The only possibility of error of said system may derive from the presence of foreign bodies inside the turbine pipe, like hairs or secretions of the patient, or fluff, coming from invisible suspensions in the air collected around the rotation axis. In both cases the measuring will be influenced by the friction that slows down, or in extreme cases might block, the movement of the mobile equipment. To these eventualities, a partial remedy is the adoption of filters upstream the mobile equipment.

The device according to the present invention responds to the need of obtaining a throwaway tester to be used by each single patient for performing a session of spirometric tests, usually consisting of a sequence of breathings. As the spirometric devices are used by a high number of different patients, sometimes afflicted with contagious breathing pathologies, if there is no throwaway tester it is at present necessary to perform long and annoying sterilization operations of that part of the tester which, during the measuring, gets into contact with the patient. The use of a throwaway tester therefore represents a considerable advantage not only for saving the time necessary for the sterilization operations, but also for the absolute hygiene guarantee offered by the same, in line with the consolidated tendency of making use of throwaway devices in the medical field, like syringes, needles, containers for organic liquids, etc.

For this purpose, throwaway testers are known at present working according to the Venturi principle, while there is no one working according to the turbine principle.

Furthermore, the testing system making use of the Venturi principle—whether throwaway or not—shows a number of disadvantages with respect to the turbine system, like:
  it gets influenced by ambient circumstances of the test, like moisture, temperature and pressure, which in turn varies according to the altitude;
  it needs a calibration at the beginning of each series of tests at determined ambient conditions;
  the electric signal is generated by a pressure transducer which usually is more expensive with respect to the infrared reader used for reading the speed in the case of a turbine system.

SUMMARY OF THE INVENTION

It is the aim of the present invention to realize a turbine device of the throwaway kind, for taking the breathing flux such as to sum the particular features of each throwaway tester with the special ones of the turbine tester, so as to show many and considerable advantages:
  an extremely restrained production cost, essential for the throwaway feature of the device;
  accuracy concerning the standards set by the ATS—American Thoracic Society
  indifference to the surrounding factors;
  interchangeability, without the need of performing each time regulation of the calibration factors;

easy insertion and removing into and from the control unity;

compatibility with a low surrounding impact;

maximum hygiene without need of any disinfection operation;

measured dimensions for reducing storing problems and transportation costs.

BRIEF DESCRIPTION OF THE DRAWINGS

The present invention will be explained more in detail hereinbelow relating to the enclosed drawings in which an embodiment is shown.

DETAILED DESCRIPTION OF THE PREFERRED EMBODIMENTS

Figure 1:
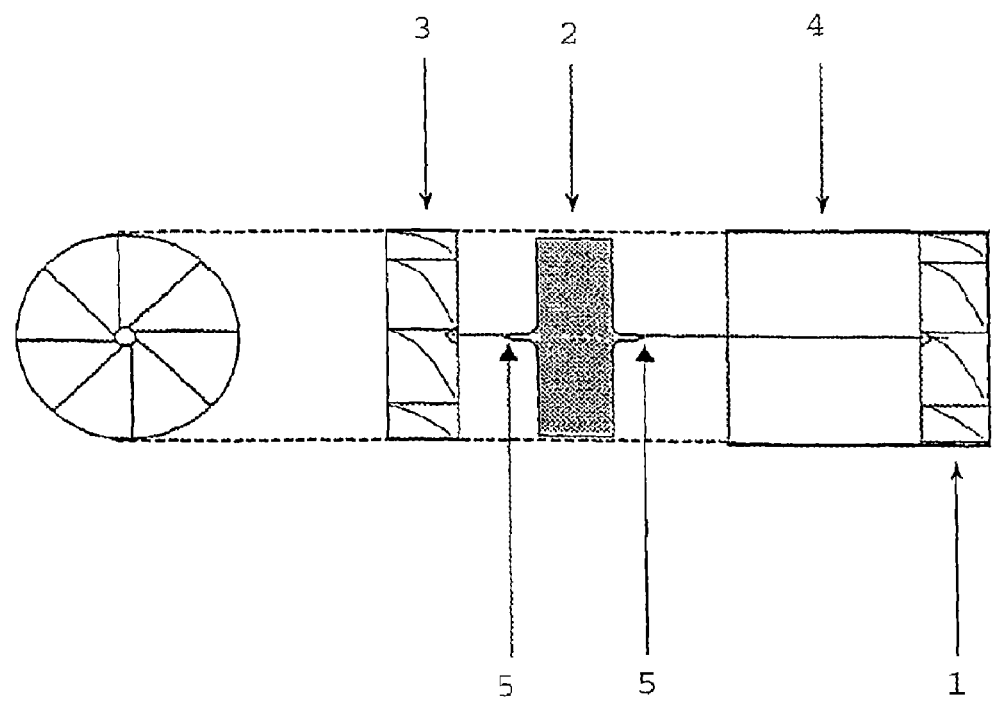
FIG. 1 shows a scheme of a throwaway turbine device for checking the breathing flux.
Figure 2:
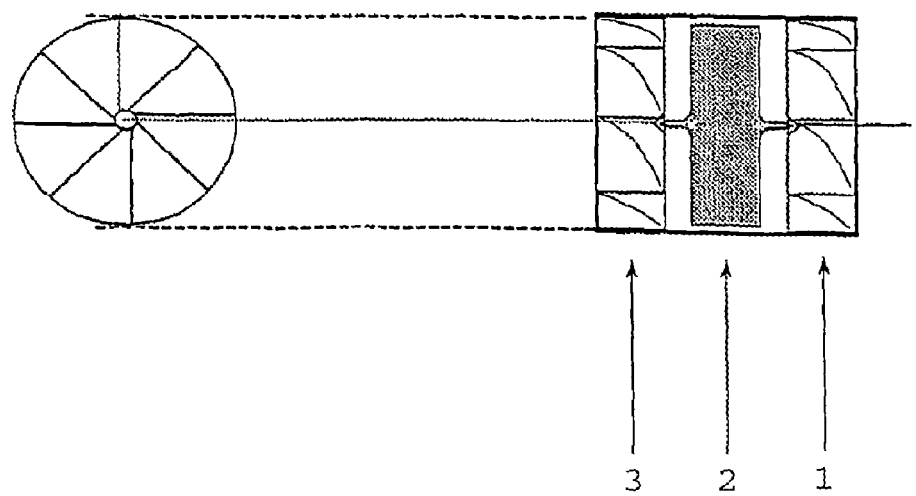
FIG. 2 shows the assembled throwaway turbine device.

The enclosed figures show a small dimension turbine device for checking the breathing flux, to be used in spirometric instruments, consisting of only three components realized in one single printing and injection production phase, making use of always the same raw material: a mobile monoblock equipment or blade 2 out of plastic material, a turbo-turbine 4 with an inlet deflector 1 and an outlet deflector 3, wherein the mobile equipment consists of one single piece comprising said blade 2 and said rotation axis 5.

It shall be underlined that the conventional turbine tester consists of eight components which require a plurality of special working phases, also because different raw materials are used, and that the mobile equipment, assembled according to the conventional turbine tester, requires a high employment of workers and use of watchmaking components.

Furthermore, the axis of the mono-block mobile equipment has a truncated-cone structure at the two ends, bevelled at 45° so that the housing of the rotation axis of said blade is realized in two cavities or seats obtained directly in the deflectors, without any other components like semi-precious stones of watchmaking.

Besides the already mentioned advantages, the present invention shows the following further advantages:

simplicity in production because no assembling or under-assembling are provided and no adjusting operation is required, as it occurs for the sapphire cavities by means of the special screws;

the technology used for the production of the throwaway tester—thermoplastic injection printing—is consolidated and allows a large scale production;

the low cost, deriving on one side from the realization simplicity and from the wide scale production technology, and on the other side from the elimination of accessory components like antibacterial filters, mouthpiece etc, vice versa necessary for the conventional turbine tester;

a greater accuracy in the measuring for an easier construction, and the elimination of under-assembling and of successive assembling, as it is known that each working phase has a determined tolerance and each of it implies risks of error;

the elimination of two factors which, in the case of the conventional turbine tester, may in time reduce the measuring accuracy: the deterioration due to the friction between the coupling surfaces of the rotation axis and the friction effect caused by the accumulation of foreign bodies, fluff etc.;

a low environmental impact deriving from a lower quantitative use of raw material and from the homogeneity of the same, which makes the recycling easier;

the simplification of performance of the spirometric test due to the elimination of any operation of sterilization, cleaning etc.

The throwaway turbine device furthermore shows considerable benefits with respect to the conventional turbine device:

absolute hygiene guarantee;

lower duration of the test because there are no dead times to be dedicated to operations like cleaning, disinfection and removing of the filters, etc.

The invention claimed is:

1. A small dimension throwaway turbine device for the checking of breathing flux, characterized in only three components realized in one single printing and injection production phase out of plastic material, making use of always the same raw material, comprising:

a mono-block mobile equipment (2), configured to rotate about a rotation axis (5), formed exclusively of a plastic material; and a turbo-turbine (4), with an inlet deflector (1) and an outlet deflector (3), the inlet deflector (1) and the outlet deflector (3) formed exclusively of the plastic material, wherein the mobile equipment consists of one single piece of the plastic material formed as a blade (2), a first extension, and a second extension, the first and second extensions extending from opposite edges of the blade along the rotation axis (5).

2. The throwaway device according to claim 1, wherein, opposite-facing ends of the first and second extensions each have a truncated-cone structure beveled with a 45° angle, and wherein the inlet deflector (1) has a first cavity directly in said inlet deflector, the outlet deflector (3) has a second cavity directly in said outlet deflector, and each of the first cavity and the second cavity are configured to house one of the first extension and the second extension.

3. The device according to claim 2, wherein the rotation axis extends through a center of the inlet deflector (1) and the outlet deflector (3).

4. The device according to claim 1, wherein said turbine is realized in one single production phase, making use of one single raw material.

5. The device according to claim 1, wherein each of the inlet deflector (1) and the outlet deflector (3) are circular, and wherein the rotation axis extends through a center of the inlet deflector (1) and the outlet deflector (3).

6. A turbine device for the checking of breathing flux, comprising:

a first deflector (1);

a second deflector (3); and a mono-block mobile equipment sandwiched between the first deflector (1) and the second deflector (3), the mono-block mobile equipment consisting of a blade, a first extension extending from a first edge of the blade, and a second extension extending form an opposite second edge of the blade, wherein the first deflector (1), the second deflector (3), and the mono-block mobile equipment are made of a same plastic material and made only of the same plastic material.

\* \* \* \* \*

UNITED STATES PATENT AND TRADEMARK OFFICE
CERTIFICATE OF CORRECTION

PATENT NO. : 7,618,235 B2 Page 1 of 1
APPLICATION NO. : 10/573899
DATED : November 17, 2009
INVENTOR(S) : Paolo Boschetti Sacco It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 502 days.

Signed and Sealed this

Fourteenth Day of December, 2010

David J. Kappos
*Director of the United States Patent and Trademark Office*